(12) United States Patent
Smith et al.

(10) Patent No.: US 9,743,977 B2
(45) Date of Patent: Aug. 29, 2017

(54) MEDICAL DEVICES WITH MULTIPLE DEGREES OF FREEDOM AND RELATED METHODS OF USE

(71) Applicants: Paul Smith, Smithfield, RI (US); Eric K. Litscher, Hopkinton, MA (US); Samuel Raybin, Marlborough, MA (US); John B. Golden, Norton, MA (US); Michael E. Zupkofska, Rockland, MA (US)

(72) Inventors: Paul Smith, Smithfield, RI (US); Eric K. Litscher, Hopkinton, MA (US); Samuel Raybin, Marlborough, MA (US); John B. Golden, Norton, MA (US); Michael E. Zupkofska, Rockland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 734 days.

(21) Appl. No.: 13/747,047

(22) Filed: Jan. 22, 2013

(65) Prior Publication Data

US 2013/0190758 A1  Jul. 25, 2013

Related U.S. Application Data

(60) Provisional application No. 61/589,495, filed on Jan. 23, 2012.

(51) Int. Cl.
*A61B 17/00* (2006.01)
*A61B 17/28* (2006.01)
(Continued)

(52) U.S. Cl.
CPC .. *A61B 18/1477* (2013.01); *A61B 17/320016* (2013.01); *A61B 17/3478* (2013.01);
(Continued)

(58) Field of Classification Search
CPC .................................................. A61B 1/00071
See application file for complete search history.

(56) References Cited

U.S. PATENT DOCUMENTS

2006/0025817 A1* 2/2006 Ortiz et al. .................... 606/219
2007/0276430 A1* 11/2007 Lee .................... A61B 1/00071
606/205
(Continued)

FOREIGN PATENT DOCUMENTS

EP  1 707 153 A1  10/2006
EP  1 866 630 A2  2/2008
(Continued)

OTHER PUBLICATIONS

International Search Report for related International Application No. PCT/US2013/022570, mailed Apr. 23, 2013, 1 page.

*Primary Examiner* — Carl H Layno
*Assistant Examiner* — Jon Eric C Morales
(74) *Attorney, Agent, or Firm* — Bookoff McAndrews, PLLC (57) ABSTRACT

Embodiments of the disclosure are directed to a medical device. The medical device may include a shaft having a proximal end and a distal end. A positioning mechanism may be disposed adjacent the distal end of the shaft. The positioning mechanism may include an outer member and an inner member coupled to an end-effector. The outer member may be pivotably attached to the distal end of the shaft and the inner member may be pivotably attached to the outer member.

15 Claims, 7 Drawing Sheets

(51) Int. Cl.
*A61B 18/14* (2006.01)
*A61B 17/32* (2006.01)
*A61B 17/34* (2006.01)
*A61B 34/00* (2016.01)
*A61B 17/29* (2006.01)
*A61B 18/00* (2006.01)

(52) U.S. Cl.
CPC .......... *A61B 18/1492* (2013.01); *A61B 34/71* (2016.02); *A61B 2017/00269* (2013.01); *A61B 2017/2927* (2013.01); *A61B 2018/0091* (2013.01); *A61B 2018/1425* (2013.01); *A61B 2217/007* (2013.01); *A61B 2218/002* (2013.01)

(56) References Cited

U.S. PATENT DOCUMENTS

2008/0039255 A1\* 2/2008 Jinno et al. .................. 474/148
2008/0188868 A1\* 8/2008 Weitzner et al. ............ 606/130

FOREIGN PATENT DOCUMENTS

| EP | 1 917 929 A1 | 5/2008 |
| EP | 2 016 913 A1 | 1/2009 |

\* cited by examiner

MEDICAL DEVICES WITH MULTIPLE DEGREES OF FREEDOM AND RELATED METHODS OF USE

This application claims the benefit of U.S. Provisional Application No. 61/589,495, filed Jan. 23, 2012, the disclosure of which is incorporated herein in its entirety.

TECHNICAL FIELD

Embodiments of this disclosure relate generally to medical devices and methods of using such devices. More particularly, embodiments of the disclosure relate to minimally invasive devices having an actuator that drives an end-effector through multiple degrees of freedom, and related methods such as, for example, endoscopic submucosal dissection.

BACKGROUND

Organ walls are composed of several layers: the mucosa (the surface layer), the submucosa, the muscularis (muscle layer), and the serosa (connective tissue layer). In gastrointestinal, colonic, and esophageal cancer, lesions or cancerous masses may form along the mucosa and often extend into the lumens of the organs. Conventionally, that condition is treated by cutting out a portion of the affected organ wall. This procedure, however, may cause discomfort to patients, and pose health risks.

Recently, physicians have adopted minimally invasive techniques called endoscopic mucosal resection (EMR) and endoscopic submucosal dissection (ESD). EMR methods are typically used for removal of small cancerous or abnormal tissues (i.e., polyps), and ESD methods are typically used for en bloc removal of large cancerous or abnormal tissues (e.g., lesions).

ESD is generally performed with an endoscope, which is a long, narrow elongated member optionally equipped with a light, imaging equipment, and other instruments. During this procedure, the endoscope is passed down the throat or guided through the rectum to reach an abnormality such as a lesion or cancerous mass in an affected organ. The lesion is identified and marked with a tissue dissection device such as, for example, an electrosurgical needle knife that is extended through a working channel of the endoscope. Submucosal injections are made at the margins of the lesion to lift the mucosa, and the lesion is removed by dissection of the submucosal tissue under the lesion using the tissue dissection device.

It has been observed that in performing these ESD procedures, physicians sweep the tissue dissection device along similar paths to remove lesions from the organ wall. Specifically, physicians sweep the tissue dissection device across and under the lesion in a planar stroke. Occasionally, an upward stroke is included at the tail end of the planar stroke.

Based on these observations, it may be beneficial to provide a tissue dissection device that follows a prescribed path and has multiple degrees of freedom so as to provide uniform tissue excision in a safe and efficient manner.

SUMMARY OF THE DISCLOSURE

One embodiment of the disclosure is directed to a medical device. The medical device may include a shaft having a proximal end and a distal end. The medical device may also include a positioning mechanism disposed adjacent the distal end of the shaft. The positioning mechanism may include an outer member and an inner member coupled to an end-effector. The outer member may be pivotally attached to the distal end of the shaft and the inner member may be pivotably attached to the outer member.

In various embodiments, the medical device may include one or more of the following additional features: wherein the inner member pivots in a first plane relative to the shaft and the outer member pivots in a second plane different than the first plane; wherein the inner member is disposed in an interior of the outer member, and wherein the end-effector extends distally from the inner member through a port in a distal face of the outer member; wherein the inner member pivots relative to the outer member to rotate the end-effector about a primary axis; wherein the outer member pivots relative to the distal end of the shaft to rotate the end-effector about a secondary axis that is different than the primary axis; further including a biasing member associated with the outer member, the biasing member being configured to control rotation of the outer member about the secondary axis; and wherein the biasing member is disposed in a plane that is not perpendicular to a longitudinal axis of the shaft.

Another embodiment of the disclosure is directed to a medical device. The medical device may include a shaft having a proximal end and a distal end. The medical device may also include a positioning mechanism disposed adjacent the distal end of the shaft and an end-effector associated with the positioning mechanism. Additionally, the medical device may include a handle connected to the proximal end of the shaft. The handle may have an actuation mechanism. A first control wire may have a proximal end connected to the actuation mechanism and a distal end connected to the positioning mechanism. A second control wire may have a proximal end coupled to the first control wire and a distal end connected to the positioning mechanism.

In various embodiments, the medical device may include one or more of the following additional features: further including a third control wire radially offset from the first control wire, the third control wire having a proximal end connected to the actuation mechanism and a distal end connected to the positioning mechanism; further including a fourth control wire radially offset from the second control wire, the fourth control wire having a proximal end coupled to the third control wire and a distal end connected to the positioning mechanism; wherein the actuation mechanism is configured to retract one of the first control wire and the third control wire so as to drive the end-effector in one of a first direction and a second direction in a first plane; and wherein the positioning mechanism is configured such that, when sufficient tension is applied to the second control wire, the outer member pivots to position the end-effector in a second plane different from the first plane; wherein the positioning mechanism is configured such that, when sufficient tension is applied to the third control wire, the outer member pivots to position the end-effector in a third plane different from the first plane; wherein the positioning mechanism includes an outer member and an inner member, wherein the outer member is pivotably attached to the distal end of the shaft, and wherein the inner member is pivotably attached to the outer member; further including a first biasing member associated with the outer member; further including a second biasing member associated with the inner member; wherein end-effector is coupled to the inner member; and wherein the first control wire and the third control wire are attached to the inner member, and wherein the second control wire and the fourth control wire are attached to the outer member.

Yet another embodiment of the disclosure is directed to a medical device. The medical device may include a shaft having a proximal end and a distal end, and a positioning mechanism pivotaby attached to the distal end of the shaft. An end-effector may be associated with the positioning mechanism. The medical device may also include a handle connected to the proximal end of the shaft. The handle may have a handle body and an actuation mechanism. The actuation mechanism may be configured to move relative to the handle body through a first position and a second position. The first position and second position may be different from each other. When the actuation mechanism is in the first position relative to the handle body, the end-effector may be in a first plane. When the actuation mechanism is in the second position relative to the handle body, the end-effector may be in a second plane.

In various embodiments, the medical device may include one or more of the following additional features: wherein the actuation mechanism is configured to move relative to the handle body through a third position different than the first position and the second position, and wherein, when the actuation mechanism is in the third position relative to the handle body, the end-effector is in a third plane; wherein the first position, second position, and third position are a single plane; wherein the positioning mechanism includes an outer member and an inner member, wherein the outer member is pivotably attached to the distal end of the shaft, and wherein the inner member is pivotably attached to the outer member; wherein the actuation mechanism is operably connected to the inner member by at least one control wire to position the end-effector in one of a first position and a second position in the first plane; further including at least one pull wire, wherein further actuation of the at least one control wire initiates actuation of the at least one pull wire to position the end-effector in the second plane; wherein the first plane and the second plane are different from each other.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate embodiments of the disclosure and together with the description, serve to explain the principles of the disclosure.

DESCRIPTION OF THE EMBODIMENTS

Reference will now be made in detail to exemplary embodiments of the disclosure, examples of which are illustrated in the accompanying drawings. Whenever possible, the same reference numbers will be used throughout the drawings to refer to same or like parts.

Figure 1:
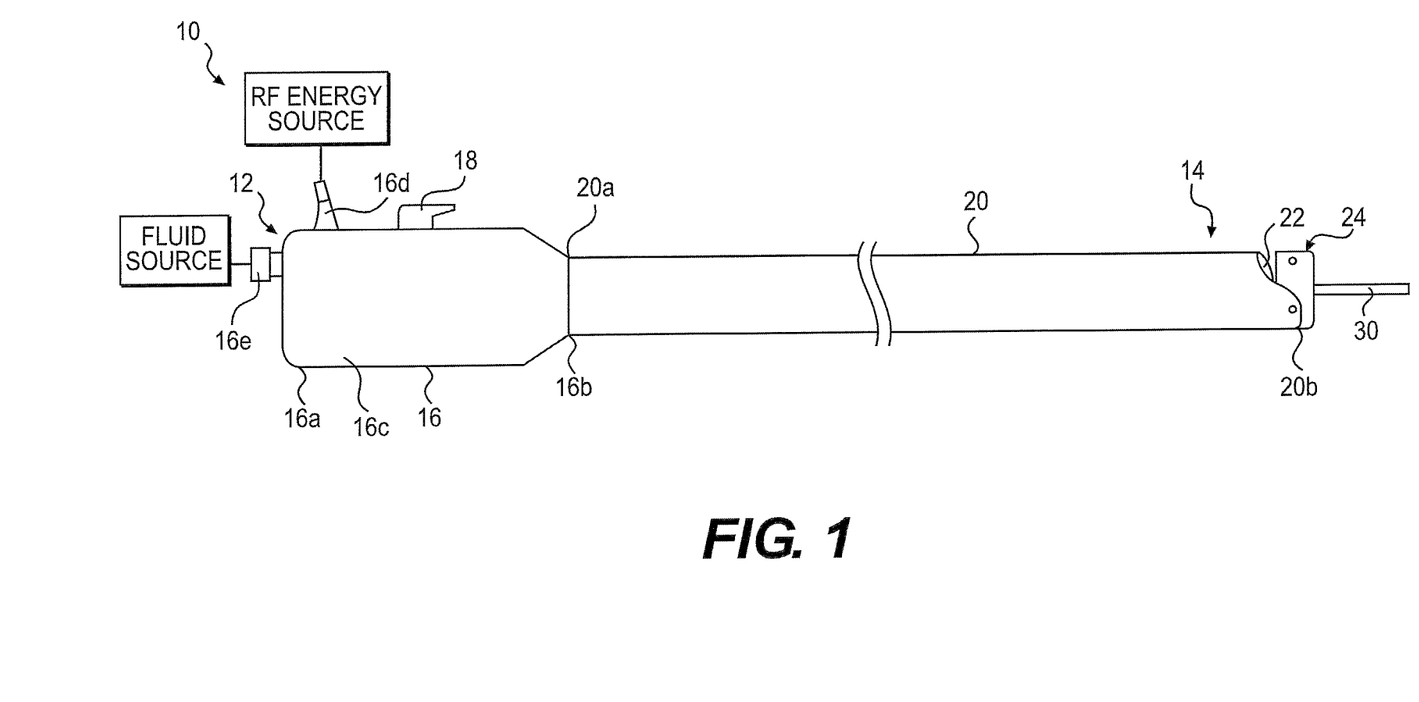
FIG. 1 illustrates a medical device having a positioning mechanism and an end-effector, according to an embodiment of the disclosure.

FIG. 1 illustrates a medical device 10, according to an exemplary embodiment. Medical device 10 may be configured for use with a surgical method, including a therapeutic or diagnostic procedure. In the exemplary embodiment, medical device 10 may be used in an endoscopic submucosal dissection (ESD) procedure for removing cancerous lesions from the mucosal walls of the colon, esophagus, stomach, duodenum, or any other location, as well as for endoscopic mucosal resection (EMR) procedures along the gastrointestinal tract. It is contemplated, however, that medical device 10 may be used in numerous other endoscopic or laproscopic procedures. For these procedures, medical device 10 may be configured for use with an endoscope or guide (not shown). It is contemplated that embodiments of the disclosure may also be applied to procedures other than the endoscopic procedures such as, for example, urological procedures, plastic surgeries, transluminal procedures, percutaneous procedures including single input laparoscopic surgery (SILS) procedures, or open invasive surgeries.

Medical device 10 has a proximal portion 12 and a distal portion 14, and includes an assembly of multiple components including a handle 16, a shaft 20, a positioning mechanism 24, and an end-effector 30 associated with positioning mechanism 24. For purposes of this disclosure, "proximal" refers to the end closer to the device operator during use, and "distal" refers to the end further from the device operator during use.

As shown in FIG. 1, proximal portion 12 includes handle 16. Handle 16 has a proximal end 16a, a distal end 16b, and an elongate body 16c extending between proximal end 16a and distal end 16b. A plurality of ports and/or connectors may be disposed on elongated body 16c of handle 16 between proximal end 16a and distal end 16b. These ports and/or connectors may connect medical device 10 to one or more external sources. In the exemplary embodiment, handle 16 includes a connector 16d to connect medical device 10 to an RF energy source (or other energy source) and a fluid port 16e to connect medical device 10 to a fluid source.

Handle 16 also includes an actuator mechanism 18 disposed on elongate body 16c of handle 16. Handle 16 and actuator mechanism 18 may be configured to allow a single hand of an operator to manipulate actuator mechanism 18 and grasp and manipulate distal portion 14 of medical device 10. In the exemplary embodiment, actuator mechanism 18 is a thumb lever configured to rotate relative to handle body 16c in a single plane. It is contemplated that actuator mechanism 18 may be a thumb wheel, a slide actuator, a button, or any other actuation mechanism known to one skilled in the art configured to move relative to handle body 16c in a single plane. As will be discussed in more detail below, actuator mechanism 18 may be operably connected to positioning mechanism 24 so as to drive end-effector 30 to positions in multiple planes. In some embodiments, a dwell or force feedback may be incorporated in handle 16 and associated with actuator mechanism 18 to provide a user with feedback when end-effector 30 changes planes.

Shaft 20 extends distally from distal end 16b of handle 16, and includes a proximal end 20a and a distal end 20b. Shaft 20 may be a flexible tube, made from any suitable biocompatible material known to one of ordinary skilled in the art, so that shaft 20 has sufficient flexibility to traverse a body cavity such as, for example, an esophagus or colon. Such materials may include, but are not limited to, rubber, silicon, synthetic plastic, stainless steel, metal-polymer composites, and metal alloys of nickel, titanium, copper cobalt, vanadium, chromium, and iron. Alternatively, shaft 20 may have a flexible design by incorporating bends, bellows, holes, cut-out portions, or any other known design. In one embodiment, the material forming shaft 20 is a superelastic material such as nitinol, which is a nickel-titanium alloy. Shaft 20 may have any cross-sectional shape and/or configuration and may be any desired dimension that can be received in an endoscope or guide. Alternatively, shaft 20 may be rigid and or dimensioned for insertion into a body cavity, without an endoscope or other guide. For example, for laparoscopy, shaft 20 may be rigid and may extend through a trocar, port, or may be percutaneously inserted.

Figure 2:
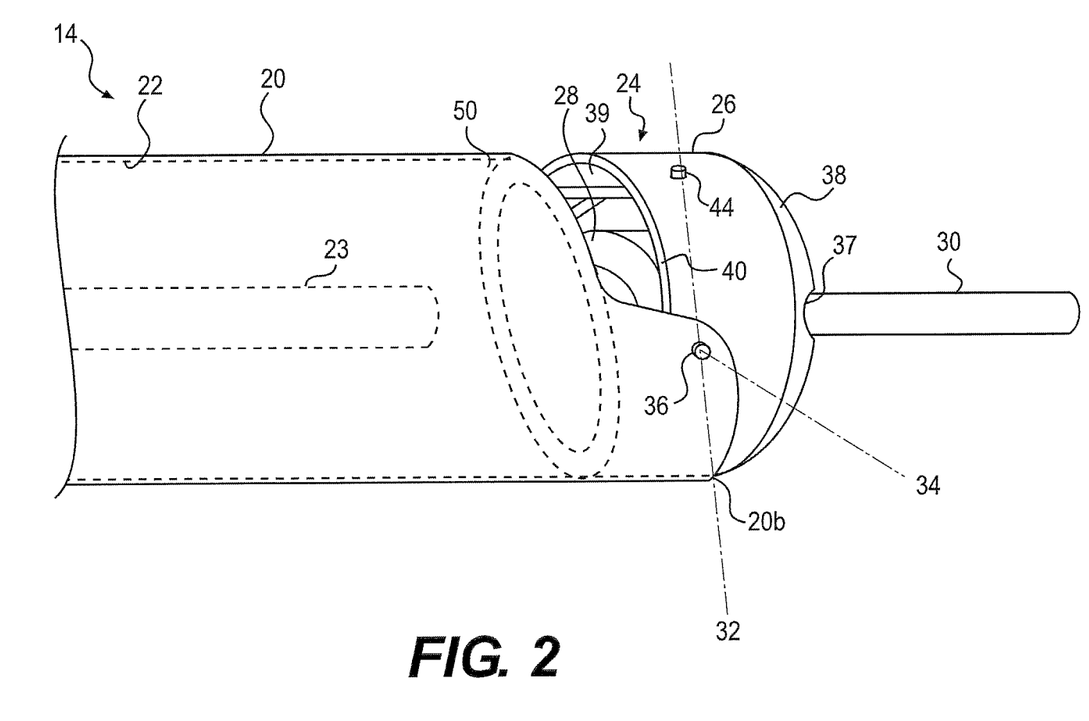
FIG. 2 illustrates a distal portion of the medical device, according to a first embodiment of the disclosure.

Shaft 20 includes a lumen 22 extending from proximal end 20a of shaft 20 to distal end 20b of shaft 20. Proximal end of lumen 22 (not shown) is in communication with an interior of handle 16. It is to be understood that lumen 22 may have any size, cross-sectional area, shape, and/or configuration. Lumen 22 is configured to receive one or more wires, cables, and/or tubes associated with positioning mechanism 24 and end-effector 30. In the exemplary embodiment, lumen 22 is configured to receive a delivery tube 23 (FIG. 2). It is appreciated that in place of delivery tube 23, an additional lumen may extend through proximal end 20a and distal end 20b of shaft 20. In those embodiments, shaft 20 may be an extruded tube having one or more lumens extruded directly into the tube.

FIG. 2 is a side view of distal portion 14 of medical device 10. As shown in FIG. 2, positioning mechanism 24 is positioned adjacent distal end 20b of shaft 20, and includes an outer member 26, a biasing spring 50, and an inner member 28. End-effector 30 may be directly coupled to inner member 28, and may be indirectly coupled to inner member 28 through outer member 26.

As will be described in more detail below, positioning mechanism 24 may be configured to pivot or deflect end-effector 30 about a primary axis 32 and a secondary axis 34 to drive end-effector 30 to positions in multiple planes. Primary axis 32 may be aligned with axial constraints 44 (e.g., pins) associated with inner member 28 and outer member 26, and secondary axis 34 may be aligned with axial constraints 36 (e.g., pins) associated with outer member 26. Primary axis 32 is shown perpendicular to secondary axis 34, and both primary axis 32 and secondary axis 34 are shown perpendicular to a longitudinal axis of shaft 20. However, primary axis 32 and secondary axis 34 may be set to any specified angle relative to the longitudinal axis of shaft 20. Additionally, it is contemplated that positioning mechanism 24 may be configured to pivot or deflect end-effector 30 about additional axes.

Outer member 26 of positioning mechanism 24 is positioned adjacent distal end 20b of shaft 20, and may be coupled to distal end 20b of shaft 20. In one embodiment, outer member 26 is disposed between surfaces of distal end 20b of shaft 20 and coupled to those surfaces by axial constraints 36, which, in some embodiments, may be located 180° apart from one another about member 26. Outer member 26 rotates about axial constraints 36, which are aligned on secondary axis 34, relative to distal end 20b of shaft 20. As shown in FIG. 2, outer member 26 is a generally cylindrical element having a distal end 38, a proximal end 40, and a hollow or compliant interior 39.

Distal end 38 of outer member 26 may be shaped to permit end-effector 30 to pivot or deflect about primary axis 32, and distal end 38 of outer member 38 may also be shaped to provide a non-sharp surface. While distal end 38 may have any shape, size, and/or configuration, in the exemplary embodiment, distal end 38 has a spherical configuration. Distal end 38 of outer member 26 includes a port 37 that is configured to receive end-effector 30. Port 37 may have any size, shape, and/or configuration to permit end-effector 30 to pivot about primary axis 32. In the exemplary embodiment, port 37 has an elongated shape that is parallel to secondary axis 34 (FIGS. 5B and 6B). In some embodiments, port 37 may permit lateral movement of end-effector 30 but may be sized to constrain end-effector 30 so that end-effector 30 moves with outer member 26 as outer member rotates about pin 36 (and secondary axis 34).

Figure 3:
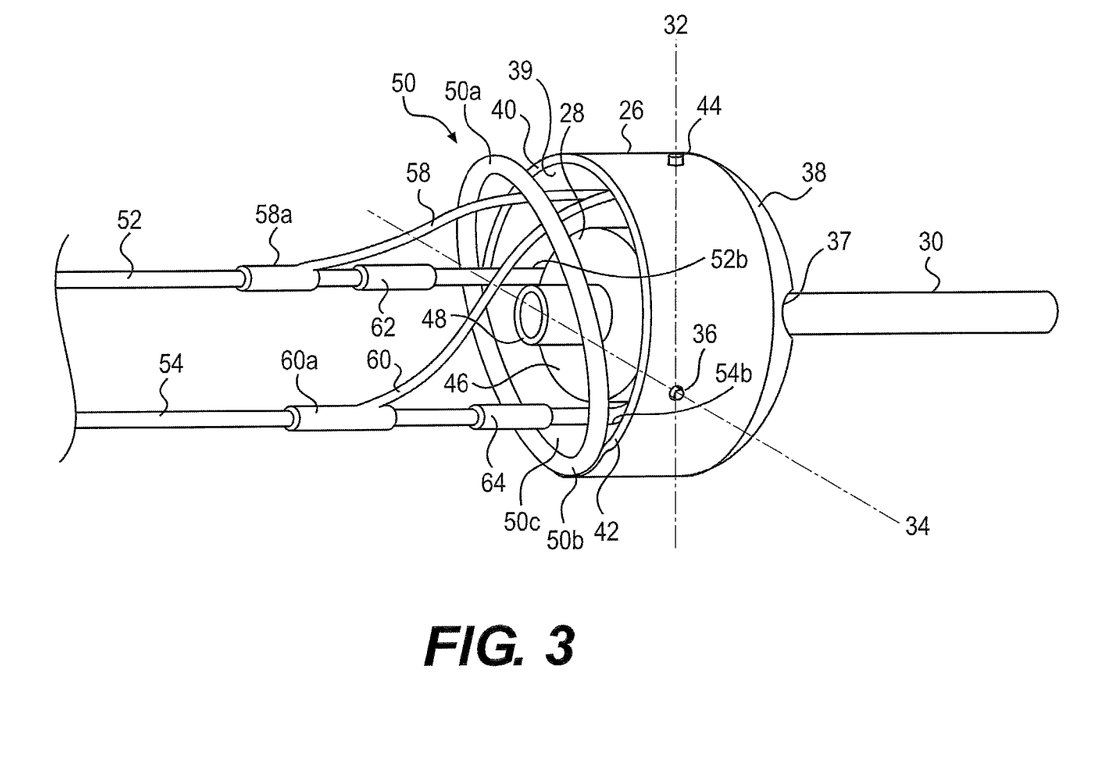
FIG. 3 is a perspective side view of the distal portion of the medical device with a shaft of the medical device and a delivery tube removed, according to a first embodiment of the disclosure.

Referring to FIG. 3, a biasing spring 50 is disposed adjacent proximal end 40 of outer member 26. Biasing spring 50 may be formed of a flexible material, which may have a ring-like shape. In some embodiments, the flexible material may be formed of a superelastic material such as nitinol, which is a nickel-titanium alloy. Biasing spring 50 has an outer diameter that is similar to an inner diameter of lumen 22, but is disposed in a plane that is not perpendicular to a longitudinal axis of the shaft 20. In particular, a first portion 50a of biasing spring 50 is position adjacent to an inner surface of shaft 20 (not shown), and a second portion 50b of biasing spring 50 is positioned adjacent to proximally facing surface 42 of outer member 26. First portion 50a is axially spaced from second portion 50b and, as shown in FIG. 3, first portion 50a of biasing spring 50 is angled away from outer member 26. Biasing spring 50 also includes an axial through hole 50c so that lumen 22 is in communication with outer member 26, inner member 28, and end-effector 30.

In this arrangement, biasing spring 50 may be configured to act as a biasing member. That is, biasing spring 50 may prevent rotation of outer member 26 about secondary axis 34 in a downward direction and limit rotation of outer member 26 about secondary axis 34 in an upward direction. It is contemplated that biasing spring may have any other shape and/or configuration such as, for example, an L-shaped spring, to prevent rotation of outer member 26 about secondary axis 34 in a downward direction.

In some embodiments, one or more biasing springs may be associated with positioning mechanism 24 to prevent rotation about each axis (i.e., primary axis 32 and secondary axis 34). In particular, a first biasing spring may be provided, similar to biasing spring 50, to limit rotation of outer member 26 about secondary axis 34 in a single direction, for example, an upward direction. A second biasing spring may also be provided to limit rotation of inner member 28 about primary axis 32 in a single direction.

Inner member 28 is disposed in interior 39 of outer member 26, and is coupled to outer member 26 by axial constraints 44, which, in some embodiments, may be located 180° apart from one another. Inner member 28 rotates about axial constraints 44, which are aligned on primary axis 32, relative to outer member 26. Rotation of inner member 28 about axial constraints 44 is independent of rotation of outer member 26 about axial constraints 36.

Inner member 28 includes a proximal end 46 and a distal end (not shown). Proximal end 46 of inner member 28 includes a fluid port 48 in communication with delivery tube 23 or another lumen of shaft 20. Fluid port 48 is also in communication with a lumen extending through the thickness of inner member 28 (not shown).

End-effector 30 is coupled to inner member 28 of positioning mechanism 24. In the exemplary embodiment, end-effector 30 extends distally from inner member 28 through port 37 formed in distal end 38 of outer member 26. In some embodiments end-effector 30 may be attached to inner member 28 by, for example, crimping, welding, or other known methods. In other embodiments, end-effector 30 may be integral with inner member 28. In yet other embodiments, end-effector 30 may extend through inner member 28 so that a portion of end-effector 30 extends proximally of proximal end 46 of inner member 28. In those embodiments, port 48 would be the proximal end of end-effector 30. Further, in those embodiments, it is contemplated that end-effector 30 moves along a longitudinal axis of shaft 12 relative to outer member 26 and inner member 28.

In the exemplary embodiment, end-effector 30 is a tissue dissection device such as, for example, a guide tub. End-effector 30 is hollow and is fluidly coupled to a delivery tube 23 through fluid port 48. In some embodiments, end-effector 30 may be a hypotube. A suitable fluid may be delivered from a fluid source in communication with fluid port 32 on handle 16 (FIG. 1) through delivery tube 23, port 48, and out of a distal opening of end-effector 30. Furthermore, end-effector 30 may be configured to deliver a separate instrument (not shown) distally of distal portion 14 of device 10. The instrument may be slidably inserted through tube 23, fluid port 48, and out of a distal opening of end-effector 30. End-effector 30 may be formed of any material capable of conducting electricity independently of the instrument. Such material may include stainless steel, nickel titanium alloys, and the like. A distal end of end-effector 30 may be relatively blunt and penetrate tissue through an electrical current running through end-effector 30. It is contemplated that other types of end-effectors may be substituted for the injection needle including, for example, knives, blades, probes, dissectors, hooks, graspers, or forceps.

Figure 4:
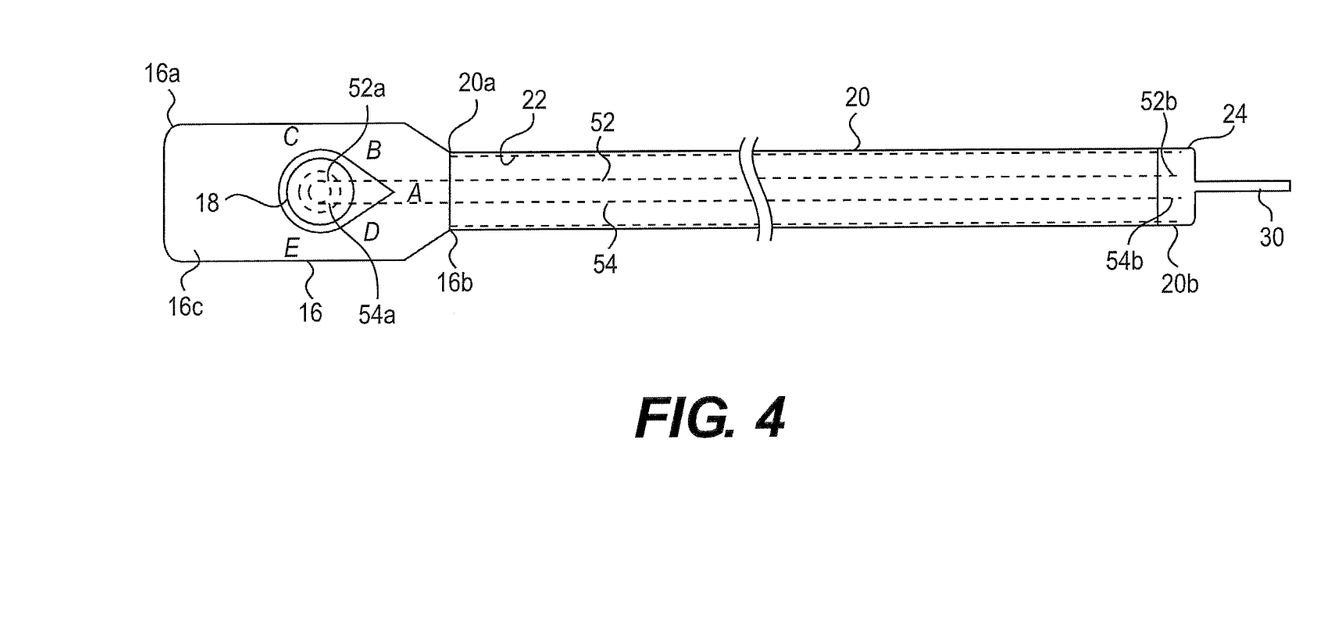
FIG. 4 is a top view of the medical device illustrating the positions of an actuator mechanism, according to a first embodiment of the disclosure.

Referring to FIGS. 3 and 4, a first control wire 52 and a second control wire 54 extend through lumen 22 of shaft 20 between inner member 28 and actuation mechanism 18 on handle 16. First control wire 52 includes a distal end 52*b* and a proximal end 52*a*. Second control wire 54 includes a distal end 54*b* and a proximal end 54*a*.

Distal ends 52*b* and 54*b* of first and second control wires 52 and 54, respectively, are attached to inner member 28. In some embodiments, distal ends 52*b* and 54*b* of first control wire 52 and second control wire 54 are aligned with axial constraints 36 and are perpendicular to axial constraints 44. As shown in FIG. 4, proximal ends 52*a* and 54*a* of first and second control wires 52 and 54 are operably connected to actuation mechanism 18 in handle 16. In an exemplary embodiment, a first sleeve 62 is fixed to first control wire 52, and a second sleeve 64 is fixed to second control wire 54 at the same axial position. Other structures such as, for example, coils, bumps, grooves, and stops may be used in place of sleeves without departing from the scope of the disclosure.

First control wire 52 and second control wire 54 are configured to pivot inner member 28 about axial constraints 44. In doing so, end-effector 30 pivots or deflects about primary axis 32 in a first direction or a second direction. As discussed above, embodiments having a second biasing member to limit rotation of inner member 28 about primary axis 32 in only one of the first direction or the second direction are contemplated. In those embodiments, a single control wire may be provided.

A first pull wire 58 and a second pull wire 60 are attached to outer member 26. In particular, distal ends (not shown) of first pull wire 58 and second pull wire 60 are attached to an inner surface (not shown) of outer member 26. In some embodiments, the distal ends of first pull wire 58 and second pull wire 60 are attached to the inner surface of outer member 26 at the same location, which is aligned with primary axis 32. In this manner, the distal ends of first pull wire 58 and second pull wire 60 are aligned with axial constraints 44 and perpendicular to axial constraints 36.

A proximal end 58*a* of first pull wire 58 may form a sleeve that is disposed about first control wire 52, and a proximal end 60*a* of second pull wire 60 may form a sleeve that is disposed about second control wire 54. Proximal ends 58*a* and 60*a* are configured to slide relative first and second control wires 52 and 54. In this arrangement, first sleeve 62 of first control wire 52 may abut first pull wire 58 or second sleeve 64 of second control wire 54 may abut second pull wire 60, respectively, to apply tension to one of first pull wire 58 and second pull wire 60. The respective pull wire may then pivot outer member 26 about axial constraints 36. In doing so, end-effector 30 may pivot or deflect about secondary axis 34. It will be appreciated that, in some embodiments, only one pull wire is required.

In an alternative embodiment, first pull wire 58 may be attached to first control wire 52 and second pull wire 60 may be attached to second control wire 54. In those embodiments, sleeves 58*a* and 60*a* and sleeves 62 and 64 may be omitted. Further actuation of either first control wire 52 or second control wire 54 may initiate actuation of first pull wire 58 or second pull wire 60.

As shown in FIG. 4, actuator mechanism 18 is connected to proximal ends 52*a* and 54*a* of first and second control wires 52 and 54. Any suitable known method of connecting control wires to actuator mechanism 18 may be used for this connection, so that rotating actuator mechanism 18 in one direction tensions first control wire 52 and rotating actuator mechanism 18 in another direction tensions second control wire 54. Actuator mechanism 18 is also indirectly connected to first pull wire 58 and second pull wire 60 through first control wire 52 and second control wire 54.

Actuator mechanism 18 may be actuated to drive end-effector 30 between positions in multiple planes. In particular, actuation mechanism 18 may move from a neutral position in a first direction through positions B and C. Position C corresponds to the most extreme position of actuator mechanism 18 in the first direction. Actuation mechanism 18 may also move from a neutral position in a second direction through positions D and E. Position E corresponds to the most extreme position of actuator mechanism 18 in the second direction. It should be appreciated that actuator mechanism 18 can be any known actuator mechanism such as, for example, a slider or a button, in which actuation in a single direction can move actuator mechanism through positions A-E.

As will be described in more detail below, the position of end-effector 30 (having similar reference letters) may be determined by the position of actuator mechanism 18 along the stroke of the actuator. In some embodiments, a user control such as, for example, a dwell or force feedback, may be incorporated in handle 16 to indicate to a user when end-effector 30 is changing positions.

Figure 5A:
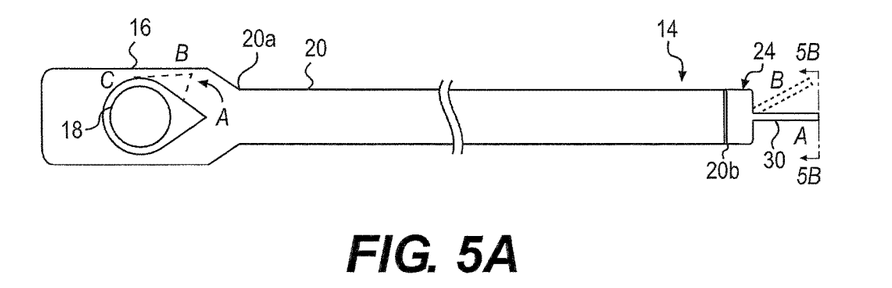
FIG. 5A is a top view of the medical device illustrating movement of the end-effector from a neutral position to a first position in a first plane, according to a first embodiment of the disclosure.
Figure 5B:
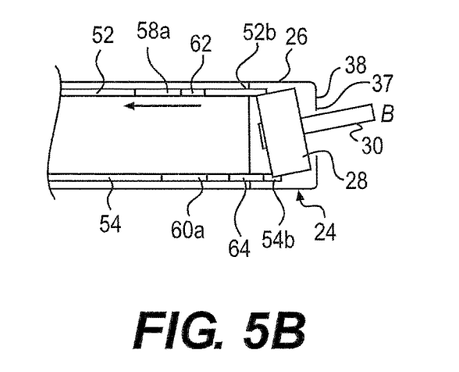
FIG. 5B is a partial cross-section of FIG. 5A with the end-effector in the first position in the first plane, according to a first embodiment of the disclosure.
Figure 5C:
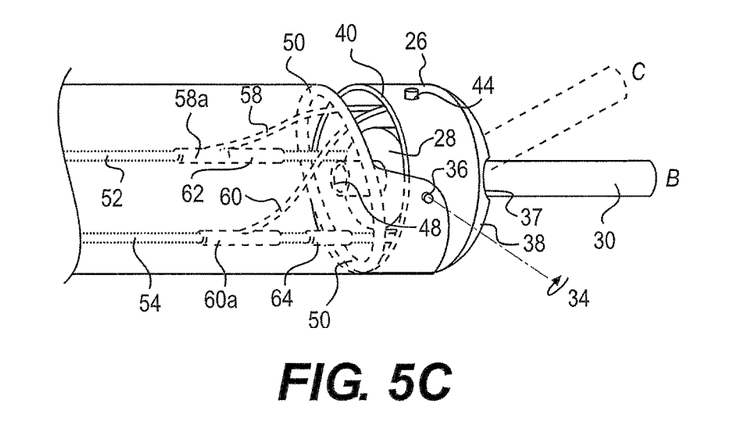
FIG. 5C is a perspective side view of the distal portion of the medical device (the shaft and delivery tube are removed) illustrating movement of the end-effector from the first position in the first plane to a position in a second plane, according to a first embodiment of the disclosure.

Referring to FIGS. 5A-5C (FIGS. 5A and 5B are top views and FIG. 5C is a perspective side view), a user may engage actuator mechanism 18 to rotate the mechanism in a first direction. In this manner, a user may retract first control wire 52 in a proximal direction. That is, first control wire 52 may be tensioned and pulled back, causing inner member 28 to rotate about axial constraints 44 relative to outer member 26. In doing so, end-effector 30 may deflect in a first direction about primary axis 32 moving from a neutral position (FIG. 5A; A) to a first position (FIGS. 5A and 5B; B) in a first plane.

When actuation mechanism 18 is rotated to its most extreme position in the first direction (i.e., position C in FIG. 5C), first sleeve 62 may engage proximal end 58*a* of first pull wire 58. Alternatively, in embodiment in which first pull wire 58 is fixed to first control wire 52, sufficient tension may be applied to first control wire 52 to actuate first pull wire 58. This may generate a force sufficient to override biasing spring 50. Outer member 26 may then rotate about axial constraints 36 relative to distal end 20*b* of shaft 20. This may pivot or deflect end-effector 30 about secondary axis 34 to move end-effector 30 from the second position in the first plane (FIGS. 5B and 5C; B) to a position in a second plane (FIG. 5C; C). Biasing spring 50 may limit rotation of outer member 26 in a single direction, for example, an upward direction. Biasing spring 50 may be further configured to return outer member 26 to a central position in the first plane, when actuator mechanism 18 is returned to the neutral position (FIG. 5A; A).

Figure 6A:
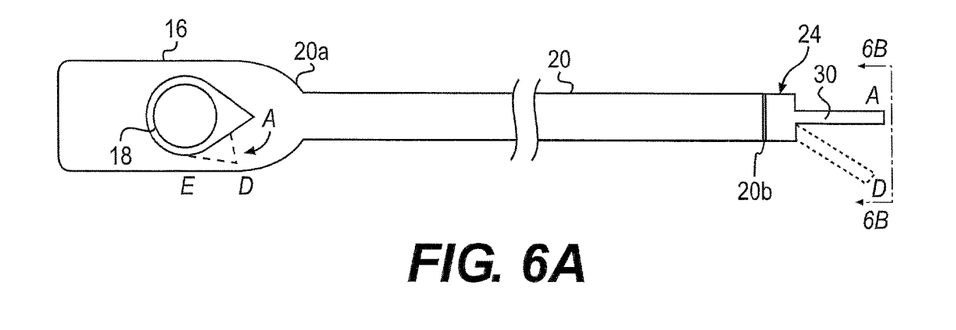
FIG. 6A is a top view of the medical device illustrating movement of the end-effector from the neutral position to a second position in the first plane, according to a first embodiment of the disclosure.
Figures 6B, 6C:
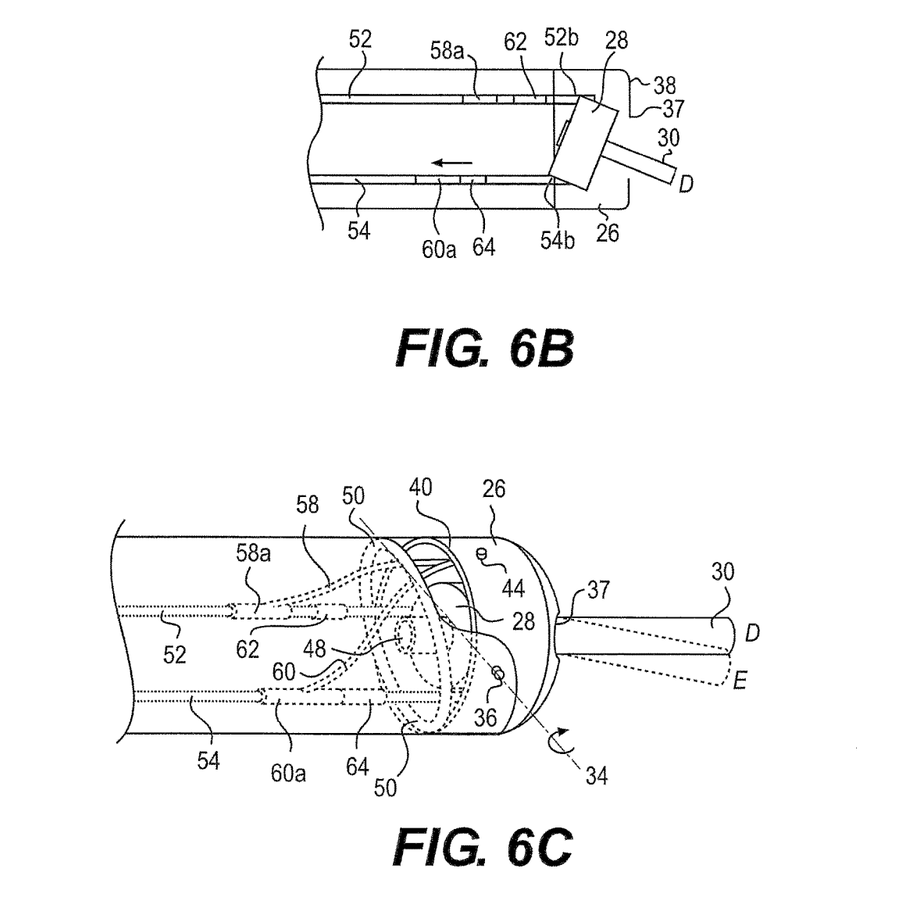
FIG. 6B is a partial cross-section of FIG. 6A with the end-effector in the second position in the first plane, according to a first embodiment of the disclosure.
FIG. 6C is a perspective side view of the distal portion of the medical device (the shaft and delivery tube are removed) illustrating movement of the end-effector from the second position in the first plane to a position in a third plane; according to a first embodiment of the disclosure.

Referring to FIGS. 6A-6C (FIGS. 6A and 6B are top views and FIG. 6C is a perspective side view), a user may engage actuator mechanism 18 to rotate the mechanism in a second direction. In this manner, a user may retract second control wire 54 in a proximal direction. That is, second control wire 54 may be tensioned and pulled back, causing inner member 28 to rotate about axial constraints 44 relative to outer member 26. This may pivot or deflect end-effector 30 about primary axis 32 to move end-effector 30 from a neutral position (FIG. 6A; A) to a second position (FIGS. 6A and 6B; D) in the first plane.

When actuation mechanism 18 is rotated to its most extreme position in the second direction (i.e., corresponding to position E in FIG. 4), the second sleeve 64 may engage proximal end 60*a* of second secondary pull wire 60. Alternatively, in embodiment in which second pull wire 60 is fixed to second control wire 54, sufficient tension may be applied to second control wire 54 to actuate second pull wire 60. This may generate a force sufficient to override biasing spring 50. Outer member 26 may then rotate about axial constraints 36 relative to distal end 20*b* of shaft 20. This may pivot or deflect end-effector 30 about secondary axis 34 to move end-effector 30 from the second position in the first plane (FIGS. 6A and 6B; D) to a position in a third plane (FIG. 6C; E). Biasing spring 50 may limit rotation of outer member 26 in a single direction, for example, an upward direction. Biasing spring 50 may be further configured to return outer member 26 to a central position in the first plane, when actuator mechanism 18 is returned to the neutral position (FIG. 6A; A).

As discussed above, end-effector 30 may be electrically conductive. For example, end-effector 30 may coagulate, cauterize, dissect, burn, and/or cut target tissue upon being energized by an electrical current. Such an electrosurgical treatment may be performed as end-effector 30 is deflected about primary axis 32 and secondary axis 34. In addition, the electrosurgical treatment by end-effector 30 may be performed in conjunction with the fluid delivery feature discussed above. For example, fluid may be injected through end-effector 30 at a tissue treatment site to separate certain tissue layers, such as a lesion from its underlying tissue. End-effector 30 may then become electrically activated and cauterize and dissect the submucosal tissue under the lesion.

In one exemplary embodiment, first and second control wires 52 and 54 may provide an electrical pathway from a source of electrical current to end-effector 30. In particular, energy from a radio frequency energy source may be configured through handle 16 via connector 16*d* to first and second control wires 52 and 54. First and second control wires 52 and 54 and inner member 28 may be formed of any material capable of conducting electricity, such as, for example, stainless steel, nickel titanium alloys, and the like. Outer member 26 may also be formed of any material capable of conducting electricity; however the surface of outer member 26 may be covered with a suitable insulating material, such as, for example, a powder coat or non-conducting polymeric sheath, to minimize the discharge and effects of any stray electrical energy from outer member 26. Insulation of outer member 26 may also prevent electrical energy from causing tissue damage due to incidental contact with outer member 26. Similarly, shaft 20 may be formed of any non-conducting polymer material, or may be coated with an insulating polymer material incapable of conducting electricity.

Figures 7A, 7B:
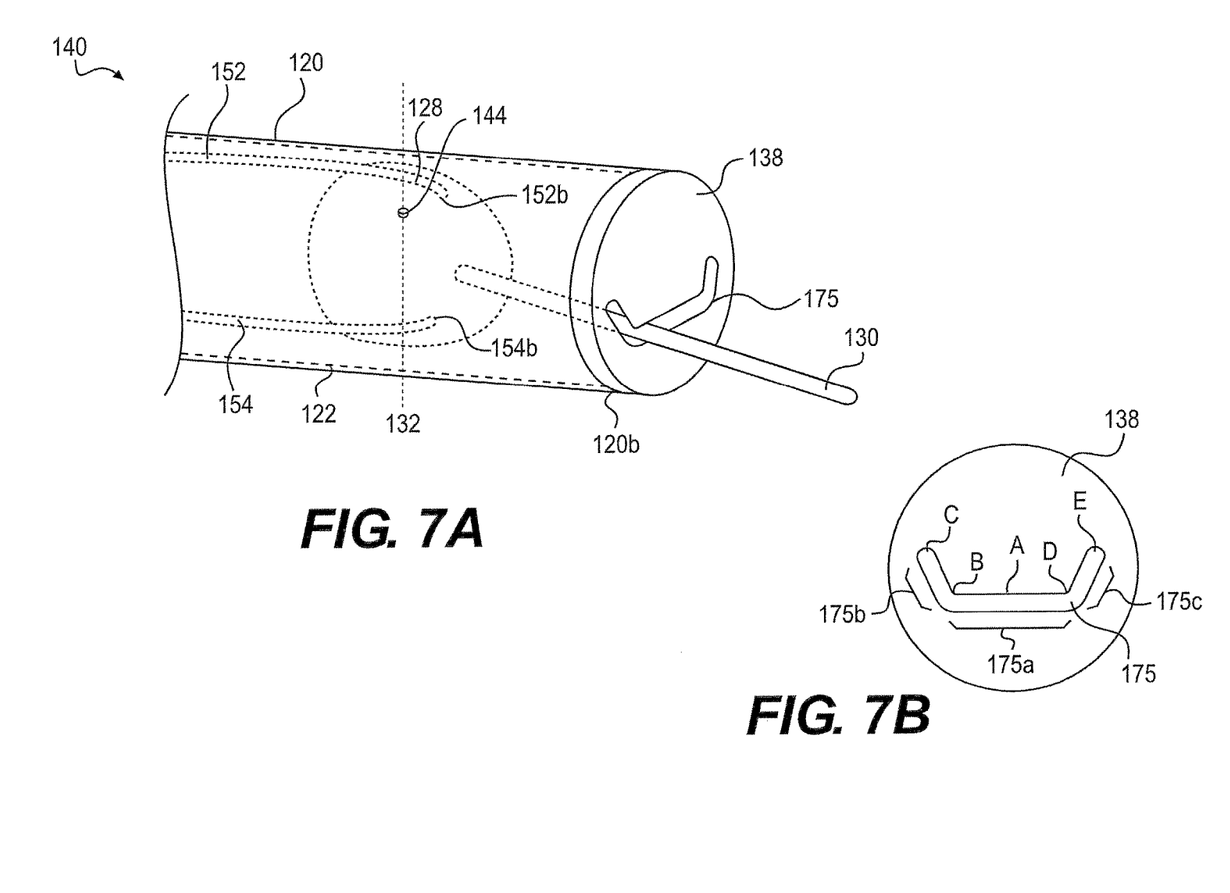
FIG. 7A is a perspective view of a distal portion of the medical device having a faceplate, in accordance with a second embodiment of the disclosure.
FIG. 7B is an end view of the faceplate, in accordance with a second embodiment of the disclosure.

FIG. 7 illustrates a distal portion 140 of medical device 10, in accordance with another embodiment of the present disclosure. Distal portion 140 includes similar components as the embodiment discussed above to drive an end-effector 130 about a primary axis 132 in a first direction or a second direction in a first plane. However, distal portion 140 includes a faceplate 138 instead of the outer member and the first and second pull wires discussed above to drive end-effector 130 into positions in a second plane and a third plane that are each different from the first plane.

In particular, the second embodiment includes a shaft 120 having a lumen 122 extending from a proximal end 120 (not shown) to a distal end 120*b*. In this embodiment, a faceplate 138 is disposed at distal end 120*b* of shaft 120. In some embodiments, faceplate 138 may be integral with shaft 120. In other embodiments, faceplate 138 may be attached to distal end 120*b* of shaft 120. Faceplate 138 is formed from a rigid material and includes a slot 175. Slot 175 may have any geometry, size, and/or configuration.

An inner member 128 is disposed in lumen 122 adjacent distal end 120*b* shaft 120. Inner member 128 is coupled to shaft 120 by axial constraints 144, which, in some embodiments, may be located 180° apart from one another about shaft 120. Inner member 128 rotates about axial constraints 144, which are aligned on a primary axis 132, relative to shaft 20.

An end-effector 130 is attached to inner member 128. In some embodiments end-effector 130 may be attached to inner member 128 by, for example, crimping, welding, or other known methods. In other embodiments, end-effector 130 may be integral with inner member 128. In the exemplary embodiment, end-effector 130 extends distally from inner member 128 through slot 175 formed in faceplate 138.

A first control wire 152 and a second control wire 154 are coupled to inner member 128, and extend proximally from inner member 128. Distal ends 152b and 154b of first and second control wires 152 and 154 are attached to inner member 128. In some embodiments, distal ends 152b and 154b of control wires 152 and 154 are attached to inner member 128 at positions that are substantially perpendicular to axial constraints 144.

Similar to the embodiment discussed above, manipulation of the first control wire 152 and second control wire 154 may cause inner member 128 to rotate about each axial constraint 144 relative to shaft 122. By doing so, end-effector 130 may swivel in primary portion 175a of slot 175 from a neutral position (A) to a first position (B) or a second position (D).

Slot 175 may be sized so as to constrain end-effector 130. In particular, slot 175 may have a diameter that is similar to end-effector 130. Rotation of end-effector 130 around the primary axis may consequently generate a reactionary force by slot 175, which may drive end-effector 130 from position B into second portion 175b of slot 175 or, alternatively, from position D into third portion 175c of slot 175. When end-effector 130 is driven to position C into second portion 175b, end-effector 130 may be positioned in a second plane that is different than the first plane. When end-effector 130 is driven to position E in third portion 175c, end-effector 130 may be positioned in a third plane that is different than the first and second planes. In this manner, end-effector 130 may be constrained to follow the prescribed path used in ESD procedures. It should be understood, however, that slot 175 of faceplate 130 may have any geometry, and end-effector 130 may follow any path defined by the geometry of slot 175. In some embodiments, the distance between faceplate 130 and axial constraints 144 may be adjustable so that the length of the sweep of end-effector 30 may be adjusted by the user.

Other embodiments of the disclosure will be apparent to those skilled in the art from consideration of the specification and practice of the features disclosed herein. It is intended that the specification and examples be considered as exemplary only, with a true scope and spirit of the disclosure being indicated by the following claims.

What is claimed is:

1. A medical device, comprising:
a shaft having a proximal end and a distal end;
a positioning mechanism disposed adjacent the distal end of the shaft, the positioning mechanism including an outer member and an inner member coupled to an end-effector, wherein the outer member is pivotably attached to the distal end of the shaft and the inner member is pivotably attached to the outer member, and wherein pivotable attachment of the outer member to the distal end of the shaft includes one or more first pins that define a first pivot axis around which the outer member pivots relative to the distal end of the shaft; and
a biasing spring configured to restrict movement of the outer member relative to the shaft.

2. The medical device of claim 1, wherein the inner member pivots in a first plane relative to the shaft and the outer member pivots in a second plane different than the first plane.

3. The medical device of claim 1, wherein the inner member is disposed in an interior of the outer member, and wherein the end-effector extends distally from the inner member through an aperture in a distal face of the outer member.

4. The medical device of claim 3, wherein the inner member pivots relative to the outer member to rotate the end-effector about an axis that is different than the first pivot axis, and wherein the outer member pivots relative to the distal end of the shaft to rotate the end-effector about the first pivot axis.

5. The medical device of claim 1, wherein the biasing spring has a first end engaging the outer member to restrict pivoting of the outer member in a direction of the first end of the biasing spring, and a second end spaced apart from the outer member to allow pivoting of the outer member in a direction of the second end of the biasing spring.

6. The medical device of claim 1, wherein the pivotable attachment of the inner member to the outer member includes one or more second pins that define a second pivot axis around which the inner member pivots relative to the outer member.

7. The medical device of claim 6, wherein the first pivot axis intersects the second pivot axis.

8. A medical device, comprising:
a shaft having a proximal end and a distal end;
a positioning mechanism disposed adjacent the distal end of the shaft;
an end-effector associated with the positioning mechanism;
a handle connected to the proximal end of the shaft, the handle having an actuation mechanism;
a first control wire having a proximal end connected to the actuation mechanism and a distal end connected to the positioning mechanism; and
a second control wire having a proximal end coupled to the first control wire and a distal end connected to the positioning mechanism.

9. The medical device of claim 8, further including a third control wire radially offset from the first control wire, the third control wire having a proximal end connected to the actuation mechanism and a distal end connected to the positioning mechanism, and further including a fourth control wire radially offset from the second control wire, the fourth control wire having a proximal end coupled to the third control wire and a distal end connected to the positioning mechanism.

10. The medical device of claim 9, wherein the actuation mechanism is configured to retract one of the first control wire and the third control wire so as to drive the end-effector in one of a first direction and a second direction in a first plane.

11. The medical device of claim 10, and wherein the positioning mechanism is configured such that, when sufficient tension is applied to the second control wire, the outer member pivots to position the end-effector in a second plane different from the first plane.

12. The medical device of claim 10, wherein the positioning mechanism is configured such that, when sufficient tension is applied to the fourth control wire, the outer member pivots to position the end-effector in a third plane different from the first and second planes.

13. The medical device of claim 9, wherein:
the positioning mechanism includes an outer member and an inner member,
the outer member is pivotably attached to the distal end of the shaft, and wherein the inner member is pivotably attached to the outer member,
the first control wire and the third control wire are attached to the inner member, and
the second control wire and the fourth control wire are attached to the outer member.

14. The medical device of claim 13, further including a first biasing member associated with the outer member, and a second biasing member associated with the inner member.

15. The medical device of claim 8, wherein the proximal end of the second control wire includes a sleeve surrounding the first control wire, and the first control wire includes an abutment configured to engage the sleeve.

\* \* \* \* \*